(12) United States Patent  
Kasai (10) Patent No.: US 7,781,641 B2  
(45) Date of Patent: Aug. 24, 2010

(54) ABSORBENT ARTICLE

(75) Inventor: Takao Kasai, Haga-gun (JP)

(73) Assignee: Kao Corporation, Tokyo (JP)

( * ) Notice: Subject to any disclaimer, the term of this patent is extended or adjusted under 35 U.S.C. 154(b) by 664 days.

(21) Appl. No.: 10/770,511

(22) Filed: Feb. 4, 2004

(65) Prior Publication Data

US 2004/0158215 A1 Aug. 12, 2004

(30) Foreign Application Priority Data

| | | | |
|---|---|---|---|
| Feb. 5, 2003 | (JP) | ............................ | 2003-028824 |
| Feb. 6, 2003 | (JP) | ............................ | 2003-030028 |
| Oct. 27, 2003 | (JP) | ............................ | 2003-366586 |
| Oct. 27, 2003 | (JP) | ............................ | 2003-366587 |

(51) Int. Cl.  
*A61F 13/15* (2006.01)  
*A61F 13/20* (2006.01)

(52) U.S. Cl. ...................... 604/367; 604/360

(58) Field of Classification Search ......... 604/367–376, 604/385.01, 387, 378, 381–382  
See application file for complete search history.

(56) References Cited

U.S. PATENT DOCUMENTS

| | | | | |
|---|---|---|---|---|
| 5,417,674 A | * | 5/1995 | Smith et al. | .................. 604/289 |
| 5,607,760 A | | 3/1997 | Roe | |
| 5,609,587 A | | 3/1997 | Roe | |
| 5,834,513 A | * | 11/1998 | Ptchelintsev et al. | ........ 514/561 |
| 5,938,649 A | * | 8/1999 | Ducker et al. | ............... 604/363 |
| 6,166,285 A | * | 12/2000 | Schulte et al. | ............... 604/364 |
| 6,685,953 B1 | * | 2/2004 | Hoshino et al. | ............. 424/401 |
| 2002/0022812 A1 | | 2/2002 | Kasai et al. | |

FOREIGN PATENT DOCUMENTS

| | | | |
|---|---|---|---|
| EP | 1 371 379 A1 | | 12/2003 |
| JP | 3217792 B2 | | 10/2001 |
| JP | 3217793 B2 | | 10/2001 |
| JP | 2002-113039 A | | 4/2002 |
| JP | 2002-200112 A | | 7/2002 |
| WO | WO 94/09757 A1 | | 5/1994 |

\* cited by examiner

*Primary Examiner*—Michele Kidwell  
(74) *Attorney, Agent, or Firm*—Birch, Stewart, Kolasch & Birch, LLP (57) ABSTRACT

The present invention provides an absorbent article capable of suppressing rash of skin in regions which come into contact with a gather portion of the absorbent article, by applying a water-soluble skin care agent and oily skin care agent on the gather portion to be contacted with the skin of a wearer in wearing the absorbent article, and allowing at least a part of the above mentioned oily skin care agent to be transferred to the skin of a wearer when wearing before the above mentioned water-soluble skin care agent is transferred to the skin of a wearer.

8 Claims, 1 Drawing Sheet

FIG1

ABSORBENT ARTICLE

This Nonprovisional application claims priority under 35 U.S.C. §119(a) on patent application Ser. No(s). 2003-028824; 2003-030028; 2003-366586 and 2003-366587 filed in JAPAN on Feb. 5, 2003; Feb. 6, 2003; Oct. 27, 2003 and Oct. 27, 2003; respectively, the entire contents of which are hereby incorporated by reference.

FIELD OF THE INVENTION

The present invention relates to absorbent articles containing a skin care agent.

BACKGROUND OF THE INVENTION

In the case of diapers, wearing time is relatively longer and several excretions are observed during this time; therefore, there is a tendency of an extreme increase in humidity inside the diaper due to sweat and excrement. Particularly, in the case of diapers having a gather portion for the purpose of suppressing leakage, close adherence to the skin is relatively higher at the gather portion and relatively lower at other portions in the diaper; consequently, there is a tendency of the skin portion in contact with the gather portion to sweat and a condition which easily causes a rash due to dampness is produced. The same phenomenon is applied also to other absorbent articles having a gather portion such as sanitary napkins, incontinence pads, panty liners, vaginal discharge sheets and the like.

There are suggestions of absorbent articles imparting a skin care effect to suppress the occurrence of rash.

For example, Japanese Patent Nos. 3217792 and 3217793 describe an absorbent product or absorbent ware having a top sheet or foot portion cuff carrying thereon an applied lotion agent containing an emollient agent and a fixing agent capable of fixing this emollient agent. Japanese Patent Application Laid-Open (JP-A) Nos. 2002-113039 and 2002-200112 describe an absorbent article in which a chemical having a predetermined efficacy is fixed or held at a predetermined site. WO 94/9757 describes a diaper having a porous sheet soaked with a skin lotion or a region soaked with a skin lotion.

Though it is possible to suppress the occurrence of rash and cure rash by previously applying a chemical such as an emollient agent, skin care agent and the like on an absorbent article, rash of the skin of a wearer may be caused in some cases also by a conventional absorbent article on which the above mentioned chemical is applied.

SUMMARY OF THE INVENTION

The present invention relates to an absorbent article having at least a liquid-impermeable outer layer sheet and an absorber fixed on the outer layer sheet and further having a gather portion having a flexible elastic member formed on at least one predetermined position, wherein a water-soluble skin care agent and an oily skin care agent are applied on a surface of the gather portion that comes in contact with the skin of a wearer, and at least a part of the oily skin care agent is capable of being transferred to the skin of a wearer when worn before the water-soluble skin care agent is transferred to the wearer's skin.

In another aspect of the present invention, there is provided an absorbent article having at least a liquid-impermeable outer layer sheet, an absorber fixed on the outer layer sheet and a liquid-permeable surface sheet covering the absorber on plane view in which a diamide derivative of the following formula (I)

(wherein, $R^1$ represents a linear or branched hydrocarbon group having 1 to 22 carbon atoms optionally substituted with a hydroxy group and/or alkoxy group, $R^2$ represents a linear or branched divalent hydrocarbon group having 1 to 12 carbon atoms, and $R^3$ represents a linear or branched divalent hydrocarbon group having 1 to 42 carbon atoms, a linear or branched alkylene group having 11 to 42 carbon atoms or an alkenylene group having 1 to 4 double bonds) is applied on the surface sheet, wherein the article has a waist flap which can be placed around the waist of a wearer when wearing the absorbent article and a leg flap which can be placed ranging from around the groin area to around the femoral area of a wearer when wearing the absorbent article, and wherein the diamide derivative is applied on the waist flap and/or the leg flap.

DETAILED DESCRIPTION OF THE INVENTION

The present invention relates to an absorbent article capable of suppressing skin rash in at least a portion of the skin which contacts a gather portion of the absorbent article. Although not wanting to be limited by theory, rash of skin can be suppressed utilizing both medicinal benefits of an oily skin care agent and a water-soluble skin care agent by applying these oily skin care agents and water-soluble skin care agents on a gather portion of the absorbent article so that at least a part of the oily skin care agent is transferred on the side of the skin of a wearer when wearing the absorbent article before the water-soluble skin care agent is transferred.

That is, in the initial stage after wearing of an absorbent article, it becomes possible to suppress rash of skin by allowing the oily skin care agent to move to the skin of a wearer to manifest its medicinal benefits, then, allowing the water-soluble skin care agent which is placed under the oily skin care agent on the absorbent article to move thereafter to the skin of a wearer to manifest its medicinal benefits.

Therefore, by using the absorbent article, it becomes possible to suppress rash of skin at least around a gather portion as compared with conventional absorbent articles.

The above mentioned diamide derivative of formula (I) is a diamide derivative described in WO 00/61097, and has medicinal benefits that the water retention ability and barrier function of a keratin layer are improved.

When this diamide derivative is applied on a predetermined surface of an absorbent article, namely, on all of or a part of the surface sheet, waist flap and leg flap which is a surface to be contacted with the skin of a wearer when wearing, this diamide derivative moves to the skin of a wearer when wearing the absorbent article, to function as an oily skin care agent. Therefore, the absorbent article can suppress rash of skin.

Embodiments of the absorbent article of the present invention, which are non-limiting examples according to the present invention, will be described specifically below referring to the drawings.

First Embodiment

Figure 1:
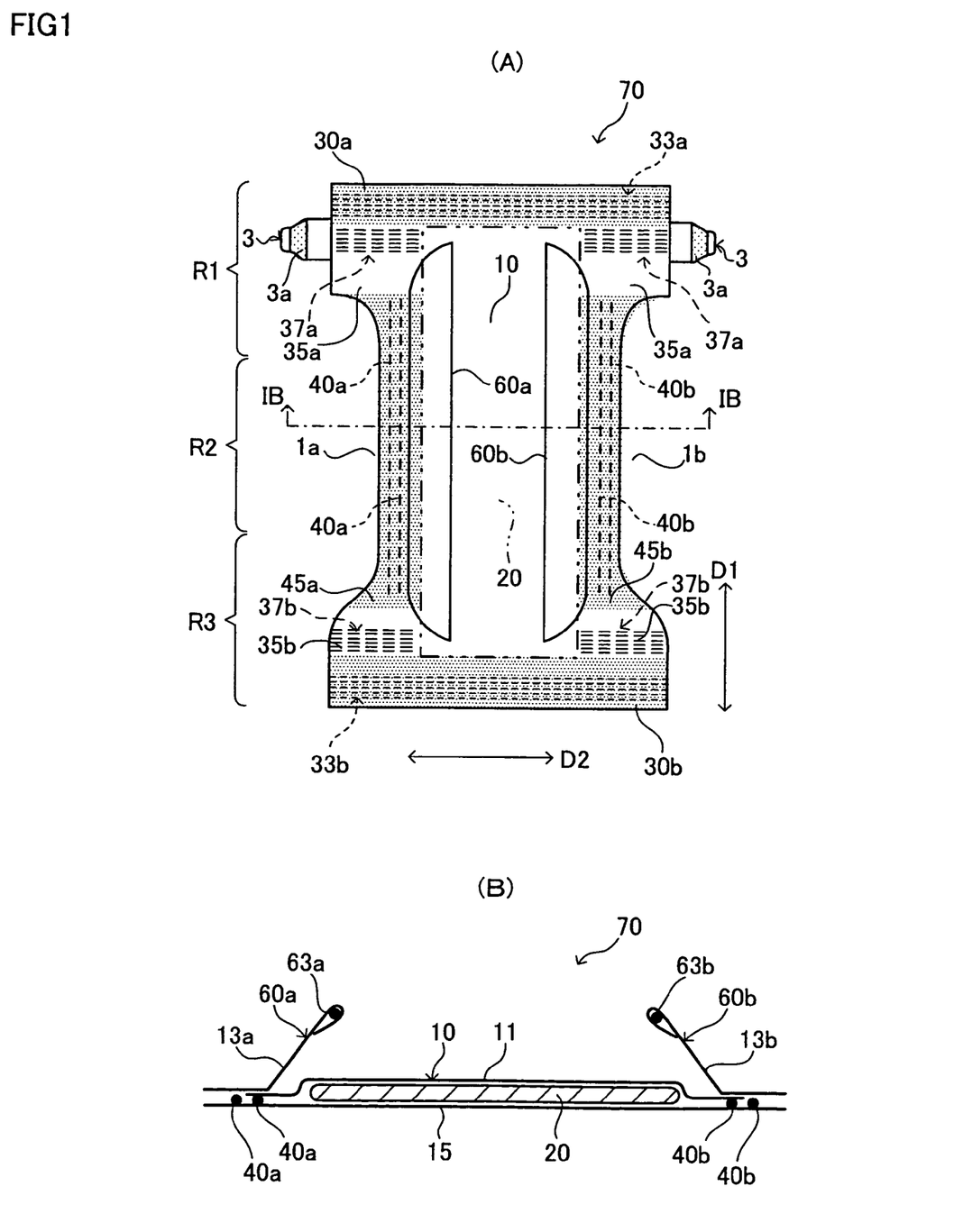
FIG. 1A is a schematic view when a diaper according to one embodiment of the present invention is kept under a tense condition and is viewed from the top view.
FIG. 1B is a sectional schematic view when the diapers shown in FIG. 1A is kept under a natural condition and is cut at positions corresponding to IB-IB line shown in FIG. 1A.

FIG. 1A is a schematic view when an absorbent article according to one embodiment of the present invention is kept under a tense condition and is viewed from the top view, and FIG. 1B is a sectional schematic view when the absorbent article shown in FIG. 1A is kept under a natural condition and is cut at positions corresponding to IB-IB line shown in FIG. 1A.

Herein, "top view" referring to the absorbent article in the present specification means a top view of an absorbent article placed so that its surface to be contacted with the body surface side of a wearer when wearing faces upward. "An absorbent article is kept under a tense condition" means that the absorbent article is kept while applying tension along its width direction and longitudinal direction so that deformation ascribable to shrinkage of an elastic body provided on the absorbent article substantially disappears.

An absorbent article 70 is an expansion type diaper (hereinafter, referred to as "diaper 70"), and can be divided, for convenience, into three regions along the longitudinal direction shown by an arrow D1 in FIG. 1A (hereinafter, referred to as "longitudinal direction D1"). One is a back side region R1 to be contacted mainly from the buttock area to the back area, another is a groin region R2 to be contacted mainly with the hypogastrium of a wearer, and further another is an abdomen side region R3 to be contacted with the stomach.

For enhancing the absorbent article's fitting property to the femoral region of a wearer and improving its mounting property, leg opening portions 1a, 1b are formed on both sides along the width direction D2 of the groin region R2, and as a result, the width of the groin region R2 is narrower than the maximum width of the other two regions R1 and R3. An edge part of the back side region R1 by the groin region R2 side and an edge part of the abdomen side region R3 by the groin region R2 side both become narrower gradually toward the groin region R2.

On separated both left and right edges along the width direction D2 of the back side region R1, a couple of members 3 in the form of tape carrying a sheet fastener convex material 3a on one surface are fixed respectively. On the rear surface (outer surface) of the abdomen side region R3, a sheet fastener concave material (not shown) made of non-woven fabric is fixed, for fixing the member 3 in the form of tape.

As shown in FIG. 1B, the diaper 70 comprises an inner sheet 10 in contact with the skin of a wearer when wearing, an outer layer sheet 15 placed on the rear side (outside) of the inner sheet 10 and an absorber 20 for absorbing excretions, and wherein the absorber 20 is placed between the inner sheet 10 and the outer layer sheet 15.

The inner sheet 10 has a liquid-permeable surface sheet 11 formed of a non-woven fabric and the like and liquid-impermeable side sheets 13a, 13b formed of non-woven fabric and the like, and wherein the surface sheet 11 covers the absorber 20 on plane view. Each one of the side sheets 13a, 13b is connected to the left edge and right edge along the width direction D2 of the surface sheet 11.

The outer layer sheet 15 is a liquid-impermeable sheet formed using an organic polymer material such as polyethylene, polypropylene, polyester and the like, and prevent leakage of excretions.

The absorber 20 is formed of an aggregate of hydrophilic fiber such as rayon, cellulose and the like, an aggregate obtained by performing a hydrophilization treatment on synthetic fiber such as polyethylene fiber, polypropylene fiber and the like, an aggregate of the above mentioned hydrophilic fiber with the above mentioned hydrophilized synthetic fiber, or absorption material layer obtained by allowing these aggregates to carry a water-absorbent polymer, and the like, or formed by wrapping the above mentioned absorption material layer with one or more of paper, non-woven fabric, porous film and the like.

The outline shape and size of the inner sheet 10 are approximately the same as the outline shape and size of the outer layer sheet 15, and by this inner sheet 10 and outer layer sheet 15, the outline shape on plane view and size of the diaper 70 excluding members 3 in the form of tape are substantially determined.

As shown in FIG. 1A, along the longitudinal direction D1, further outer regions than the longitudinal direction end of the absorber 20 are composed of waist flaps 30a, 30b placed around the waist of a wearer in wearing. And outer regions than the width direction end of the absorber 20 in regions nearer to the waist flaps 30a, 30b than the leg opening portions 1a, 1b are composed of peripheral flaps 35a, 35b placed around peripheral regions of the body of a wearer in wearing. Therefore, the back side region R1 and abdomen side region R3 have respectively the waist flap 30a or 30b and peripheral flap 35a or 35b. In FIG. 1A, the waist flap 30a in the back side region R1 and the waist flap 30b in the abdomen side region R3 are illustrated with shading.

On the waist flap 30a, several flexible elastic members 33a (hereinafter, referred to as "waist elastic member 33a") are placed so as to extend along the width direction D2. At the same time, on the waist flap 30b, several flexible elastic members 33b (hereinafter, referred to as "waist elastic member 33b") are placed so as to extend along the width direction D2.

As these waist elastic members 33a, 33b, for example, thread rubber, flat rubber and the like may be used, and all of the waist elastic members 33a, 33b are fixed under a tense condition between the inner sheet 10 and the outer layer sheet 15. Therefore, when the diaper 70 is in a natural condition or the diaper is worn, the waist elastic members 33a, 33b shrink relatively to form waist gather portions on the waist flaps 30a, 30b respectively.

In this embodiment, several flexible elastic members 37a or 37b (hereinafter, referred to as "peripheral elastic members 37a, 37b") are placed on the peripheral flaps 35a, 35b respectively. Further, on the left portion (left portion in FIG. 1A) of the absorber 20 seen along the width direction D2, several flexible elastic members 40a (hereinafter, referred to as "leg elastic member 40a") are placed so as to extend along the longitudinal direction D1, and on the right portion (right portion in FIG. 1A) of the absorber 20, several flexible elastic members 40b (hereinafter, referred to as "leg elastic member 40b") are placed so as to extend along the longitudinal direction D1.

Also as the above mentioned peripheral elastic members 37a, 37b and the leg elastic members 40a, 40b, thread rubber, flat rubber and the like may be used like the waist elastic members 33a, 33b, and all of the elastic members 37a, 37b, 40a, 40b are fixed under a tense condition between the inner sheet 10 and the outer layer sheet 15. Therefore, when the diaper 70 is in a natural condition or the diaper is worn, the peripheral elastic members 37a, 37b shrink relatively to form peripheral gather portions, and the leg elastic members 40a, 40b shrink relatively to form leg gather portions. The leg gather portions are allowed to contact with from around the groin region to around the femoral region of a wearer in wearing.

In FIG. 1A, the region in which a leg gather portion is formed by the leg elastic member 40a is represented by reference mark 45a, and the region in which a leg gather portion is formed by the leg elastic member 40b is represented by reference mark 45b, and these regions are illustrated with shading. However, each range of the illustrated regions 45a, 45b is not strict and roughly defined.

The diaper 70 has standing guards 60a, 60b which are a gather portion placed near the absorber 20, in addition to the above described each gather portion. These standing guards 60a, 60b are all provided along the longitudinal direction D1 of the diaper 70.

The illustrated standing guards 60a, 60b are formed by adhering the side sheet 13a or 13b (see FIG. 1B) to a part of the surface sheet 11 to make a fixed end, and fixing the flexible elastic member 63a or 63b extending along the longitudinal direction D1, in extended condition, to the inside of a region as a free end (far end from the outer layer sheet 15), so as to project to the direction of a wearer. In wearing, the free end portion is projected to the side of the skin of a wearer, to form a standing gather portion.

The feature of the diaper 70 of the present invention is that a water-soluble skin care agent and an oily skin care agent are applied in a predetermined pattern on at least one of the above mentioned gather portions.

In this embodiment, a water-soluble skin care agent is applied on the respective inner surfaces (surface of the side to be contacted with the skin of a wearer in wearing) of the waist flaps 30a, 30b, peripheral flaps 35a, 35b, regions 45a, 45b, standing guards 60a, 60b, and an oily skin care agent is applied thereon.

The above mentioned water-soluble skin care agent and oily skin care agent will be explained sequentially below.

(A) Water-Soluble Skin Care Agent

The water-soluble skin care agent is preferably one which has water-solubility or water-dispersibility, suppresses the occurrence of rash and inflammation, and, when rash or inflammation occurs, suppresses progress of the rash or inflammation, or relaxes the rash or inflammation.

Specific examples of the water-soluble skin care agent include (1) various plant extracts, (2) collagens, (3) humectants such as natural moisturizing factors (NMF), 1,3-butylene glycol, propylene glycol, dipropylene glycol, glycerin and the like, (4) keratin softening agents such as arginine, guanidine derivatives (for example, organic acid salts (for example, succinate, glycolate, lactate, malate, citrate, tartarate and the like) of 2-(2-hydroxyethoxy) ethylguanidine), and the like, (5) antiphlogistics such as guaiazulene, tannin, gallic acid derivatives and the like.

In view of solubility in water, skin care effect and cost, it is preferable to use, as the water-soluble skin care agent, plant extracts or natural moisturizing factors (NMF).

Specific examples of the above mentioned plant extract include oat extract, sea weed (Fucus) extract, citrus extract, hamamelis (*Hamamelis virginiana*) extract, burnet extract, hiba arborvitae extract, aloe extract, phellodendron bark powdered extract, field horsetail extract, chamomilla redutita extract, eucalyptus extract, peach leaf extract and the like. Particularly, a higher skin care effect can be obtained by using citrus extract, hamamelis extract, hiba arborvitae extract, aloe extract, phellodendron bark powdered extract, eucalyptus extract or peach leaf extract.

When a highly water-absorbing polymer is used as a material of absorption bodies, it is preferable that degradations such as deterioration of the absorbing performance of the highly absorbing polymer and the like are not caused by the above mentioned water-soluble skin care agent, and for this purpose, it is preferable to use, as a water-soluble skin care agent, citrus extract, hamamelis extract, hiba arborvitae extract, aloe extract, phellodendron bark powdered extract, or peach leaf extract, particularly, citrus extract, hamamelis extract or hiba arborvitae extract.

Plant extracts can be obtained by, for example, drying the whole bodies of various plants or one or more parts of leaf, bark, root and branch thereof, grinding them alternatively without drying, and extracting them under normal temperature or heating by a solvent, or extracting them using an extraction instrument such as a Soxhlet extractor and the like. When a 1,3-butylene glycol extract is used as a plant extract, solubility in water increases, and additionally, it is not necessary to prepare the protection for explosion even if the heating treatment is conducted in a process of producing fiber or absorbent articles. Further, when it is applied on a surface sheet or a sheet or fiber as a material of the surface sheet, a decrease in the absorbing performance of an absorber constituting an absorbent article is suppressed.

Usually, a plant extract contains solvent components and water used for extraction in addition to effective components. In this condition, the amount of effective components (amount excluding evaporation solvent components and water) of a plant extract may be advantageously from about 0.001 to 5 wt %. When 1,3-butylene glycol is used as a solvent component for extraction, the sum amount of effective components of a plant extract and 1,3-butylene glycol may be advantageously in the above mentioned range. The amount of effective components in a plant extract is preferably from about 0.001 to 10 wt % based on the amount of solvent components.

It is preferable that the above mentioned water-soluble skin care agent is fixed on a predetermined part (the waist flaps 30a, 30b, peripheral flaps 35a, 35b, regions 45a, 45b, and standing guards 60a, 60b, in the diaper 70 shown) of an absorbent article under condition releasable with water, and particularly, it is preferable that the abovementioned water-soluble skin care agent is fixed on an absorbent article under condition dissolvable or dispersible in excretions or sweat by contact with the urine, feces, menstrual blood, vaginal discharge and the like (hereinafter, these are generically called "excretions"). When the water-soluble skin care agent is present on an absorbent article under such condition, this water-soluble skin care agent easily moves to the skin of a wearer in wearing an absorbent article; therefore, the effect is easily manifested.

Here, "fixed under condition releasable with water" used for a water-soluble skin care agent in the present specification means that this water-soluble skin care agent has high water-solubility or water-dispersibility. For example, "fixed under condition releasable with water" is established if, when a sheet on which a water-soluble skin care agent is fixed is soaked in water (liquid temperature: 25° C.) in an amount of 10 times of the weight of this sheet, and the water-soluble skin care agent is substantially dissolved or dispersed.

It is advantageous that a water-soluble skin care agent can move from an absorbent article to the skin of a wearer using water as the main means, or a water-soluble skin care agent may move to the skin of a wearer using an auxiliary means other than water.

Fixing of a water-soluble skin care agent to an absorbent article can be conducted, for example, by applying liquid coating (agent) containing a water-soluble skin care agent on a predetermined position of the surface sheet or inner sheet or a sheet as a material of these sheets, and drying the liquid.

In the present invention, it is preferable that the above mentioned coating liquid contains a surfactant, particularly at the waist gather portion. By this, in a stage before perspiration or excretion, a water-soluble skin care agent is fixed stably on the surface of an inner sheet; therefore, it is possible to suppress movement of both the water-soluble skin care agent and oily skin care agent to the skin of a wearer directly after wearing. Additionally, simultaneous use of a surfactant has merits also in hydrophilicity, repeating absorbability of an absorber in an absorbent article, or rust prevention for a facility of producing non-woven fabric and absorbent articles, and non-woven fabric processability and the like.

When excretion occurs, a large proportion of water-soluble skin care agent moves to the side of an absorber together with a surfactant, and in this phenomenon, a part of the water-soluble skin care agent moves to the side of the skin of a wearer. Therefore, even if excretions come into contact with skin, a water-soluble skin care agent protects skin, and the occurrence of rash is suppressed or relaxed. Further, since movement of a water-soluble skin care agent to skin easily occur during perspiration or excretion, even if, for example, humidity in an absorbent article increased by absorption of excretions and this condition lasts for a long period of time, it is possible to allow the skin care effect of a water-soluble skin care agent to continue sufficiently. As a result, the skin of a wearer is protected by this skin care effect, and the occurrence of rash is suppressed or relaxed.

Fixing of a water-soluble skin care agent to an absorbent article can also be conducted, when the subject on which the water-soluble skin care agent is to be fixed is a non-woven fabric, by previously fixing a water-soluble skin care agent to fiber constituting non-woven fabric and producing non-woven fabric using this fiber as a material. In this case, fixing of a water-soluble skin care agent can be conducted, for example, by preparing a liquid coating containing a water-soluble skin care agent and containing a surfactant and a fiber treating agent such as a higher alcohol or the like added if necessary, and adhering this liquid coating to the above mentioned fiber by a method such as dipping, spray coating, roll coating and the like, then, drying the fiber.

In the case of fixing by any method, a water-soluble skin care agent may be continuously adhered in the form of a membrane or layer on the surface of a fixation subject, or may be adhered discontinuously (for example, in the form of a particle or a discontinuous film).

The suitable fixing amount of a water-soluble skin care agent differs depending on the kind of a water-soluble skin care agent used, and can be appropriately selected in a range which does not cause deterioration to the skin. When the fixing amount of a water-soluble skin care agent is too large, the skin care effect is saturated; therefore, it is preferable to determine the upper limit of this fixing amount in view of the skin care effect and economy. For example, when a plant extract is used as a water-soluble skin care agent and this water-soluble skin care agent is fixed on the surface of the fiber, the fixing amount preferably is from about 0.01 to 5 wt %, more preferably from about 0.5 to 2 wt %.

For fixing a water-soluble skin care agent to a region formed of hydrophobic fiber, such as the waist flaps 30a, 30b shown in FIG. 1A, under condition releasable by water, it is preferable to used a water-soluble skin care agent and a surfactant together, and it is further preferable to used 1,3-butyleneglycol together. Though 1,3-butylene glycol can be used as a water-soluble skin care agent itself as described above, it is particularly preferable, when a plant extract is used as a water-soluble skin care agent, to use this 1,3-butyleneglycol as a solvent for fixation of the plant extract to the surface of the fiber.

As the surfactant to be contained in the above mentioned coating liquid, any of the anionic surfactants, cationic surfactants and nonionic surfactants can be used. Specific examples thereof include polyoxyethylene alkyl sulfate metal salts, alkyl sulfate metal salts, polyoxyethylene alkyl phosphate metal salts, alkyl phosphate metal salts, fatty diethanol amide, fatty sorbitan esters (may be any of mono, di and triester), alkyl glucoside, polyglycerin fatty esters, alkyl succinate metal salts and the like. As the above mentioned metal salts, for example, sodium salts and potassium salts can be used.

The surfactant may be used alone or in combination of two or more surfactants. In view of hydrophilicity, repeating absorbability of an absorber in a diaper, or rust prevention for facilities which produce non-woven fabric and diapers, and non-woven fabric processability and the like, it is particularly preferable to use, as the surfactant, one or more of polyoxyethylene alkyl phosphate metal salts, alkyl phosphate metal salts, fatty diethanol amide, fatty sorbitan esters, alkyl glucoside, and alkyl succinate metal salts.

From the standpoint of fixing stably a water-soluble skin care agent to the surface of the hydrophobic fiber, it is preferable to use a hydrophobic surfactant and a hydrophilic surfactant in admixture. For example, when two or more nonionic surfactants are used in admixture, HLB (hydrophilicity lipophilicity balance) can be used as an index. When a hydrophilic surfactant having a HLB of 8 or more, particularly 10 or more and a hydrophobic surfactant having a HLB of 6 or less, particularly 5 or less are used in admixture at a mixing ratio of hydrophilic surfactant/hydrophobic surfactant of about 90/10 to 30/70 (wt %), fixing of a water-soluble skin care agent with a sheet produced using hydrophobic fiber as the main material is stabilized, and even if an oily skin care agent is released by contact with the skin of a wearer directly after wearing of an absorbent article, the water-soluble skin care agent tends to remain on the surface sheet. Additionally, the water-soluble skin care agent is easily released from the surface of the surface sheet after exposure to excretion.

In the above mentioned coating liquid, in addition to the surfactants and fiber treating agents, there can be formulated anti-static agents, antioxidants, pH regulators, smoothing agents, emulsifiers, antimicrobial agents, antifungal agents, aromatics and the like.

(B) Oily Skin Care Agent

As the oily skin care agent, those having efficacies such as protection, cure and the like for the skin of a wearer can be used without specific restriction, and for example, those used as an emollient agent in the field of cosmetics can be used.

Specific examples of the oily skin care agent include liquid paraffin, silicone oil, animal and vegetable oil (olive oil, jojoba oil, safflower oil, squalane and squalene, and the like), monoglyceride, diglyceride, triglyceride, aliphatic ether (myristyl-1,3-diemthyl butyl ether, palmityl-1,3-dimethyl butyl ether, stearyl-1,3-dimethyl butyl ether, palmityl-1,3-methyl propyl ether, stearyl-1,3-methyl propyl ether and the like), and isostearyl cholesterol ester and the like.

Further, paraffin wax, $C_{12}$ to $C_{22}$ fatty acids, $C_{12}$ to $C_{44}$ fatty ethers, $C_{12}$ to $C_{22}$ fatty alcohols, vaseline, metal soap (magnesium stearate, and the like), sucrose fatty ester, cyclodextrin fatty ester, silicone resin, alkyl silicone, silicone, fatty sorbitan ester (may be any of monoester, diester and triester), polyoxyethylene fatty sorbitan ester (may be any of monoester, diester and triester), and emollient agents used in inventions described in Japanese Patent No. 3217792, JP-A Nos. 2002-113039 and 2002-200112, WO 94/9757, and the like can also be used as the above mentioned oily skin care agent.

Further, it is also possible to use, as an oily skin care agent, adiamide derivative of the following formula (I) described in WO 00/61097:

(I)

(wherein, $R^1$ represents a linear or branched hydrocarbon group having 1 to 22 carbon atoms optionally substituted with a hydroxy group and/or alkoxy group, $R^2$ represents a linear or branched divalent hydrocarbon group having 1 to 12 carbon atoms, and $R^3$ represents a linear or branched divalent hydrocarbon group having 1 to 42 carbon atoms, a linear or branched alkylene group having 11 to 42 carbon atoms or an alkenylene group having 1 to 4 double bonds).

An oily skin care agent plays mainly a role that it reduces friction of a gather portion and the skin of a wearer, and additionally, it moves to the skin of a wearer by the fastening force of the gather, to suppress direct contact of excretions to the skin of a wearer. By this, it suppresses the occurrence of rash by relaxing friction with a gather and stimulation by excretions. Therefore, this oily skin care agent is applied on a predetermined region of a sheet or absorbent article on which a water-soluble skin care agent is applied (fixed).

In this embodiment, it is preferable to use oily skin care agents having a viscosity at 36° C. of 5000 mPa·s or less, more preferably from 200 to 5000 mPa·s, even more preferably from 500 to 2000 mPa·s, or those of which viscosity is controlled to obtain such viscosity.

By using an oily skin care agent having a viscosity as described above, the oily skin care agent can be effectively moved to the skin of a wearer. That is, when the viscosity of an oily skin care agent is 5000 mPa·s or less, the property of moving to the skin becomes extremely excellent, and there is no necessity to use an oily skin care agent in a large amount for realizing a desired rash suppressing effect. Further, its influence on absorbability decreases. When the viscosity of an oily skin care agent is 200 mPa·s or more, movement of an oily skin care agent to other sites can be effectively prevented even in the case of preservation over a long period of time of an absorbent article before wearing; as a result, a predetermined skin care effect is obtained effectively.

"Viscosity of an oily skin care agent" in the present invention means viscosity measured as described below.

<Method of Measuring Viscosity>

Measurement is conducted using a tuning fork type vibration mode viscometer (VIBRO NISCOMETERCJV5000 (manufactured by A&D Company Limited) is typically used in this embodiment). An oily skin care agent heated previously at about 100° C. is gradually cooled to room temperature, and viscosity at the predetermined temperature is measured.

The oily skin care agent used in the present invention preferably shows smaller dependency of viscosity on temperature. Specifically, preferable are those having a viscosity at 36° C. within the above mentioned range and a viscosity at 80° C. of from 50 to 200 mPas. When dependency of viscosity on temperature is small, an oily skin care agent can be uniformly applied easily on a surface sheet, and it is stably fixed on a surface sheet even if some temperature change occurs; consequently, there is a scarce tendency of the occurrence of absorption disturbance by penetration or diffusion of an oily skin care agent in an absorber. Further, a two-stage skin care effect tends to be manifested in which an oily skin care agent moves first to the skin of a wearer, then, a water-soluble skin care agent moves to the skin of a wearer.

Application of an oily skin care agent on an absorbent article or its material can be conducted, for example, by putting the oily skin care agent into a tank of an applicator, and if necessary, heating this to enhance its flowability, then, coating this on a predetermined position on a diaper or its material.

As the method of coating an oily skin care agent, preferred are a dice coater method, slot spray method, curtain spray method, melt blown method, spiral spray method, gravure method, bead method and the like.

When a method of spraying with air is used as in a spray method, an oily skin care agent is converted into fine particles or mist and sprayed on the surface of an application subject. For this reason, an oily skin care agent is continuously provided macroscopically on a surface sheet, while microscopically, the agent is distributed discontinuously on the surface of an application subject.

As a result, it becomes possible to secure the liquid permeability of a surface sheet and effectively utilize the absorbing ability of an absorber while performing a skin care effect in a wider range. Application of an oily skin care agent by a method of spraying with air is suitable for obtaining a predetermined absorbent article. Of course, in the case of applying a method of spraying with air, the form of an application region with an oily skin care agent can be desired in patterns such as a stripe, lattice and the like.

In view of a skin care effect, feeling and the like, the application amount of an oily skin care agent (meaning application amount on a region on which an oily skin care agent is actually applied) is preferably in the range from 0.05 to 20 $g/m^2$, more preferably in the range from 0.1 to 10 $g/m^2$, depending on the kind and application pattern of the oily skin care agent used. This application amount can be determined from a difference in weight of an application subject before and after application of an oily skin care agent.

If necessary, two kinds of application methods can be used together in one absorbent article. For example, a dice coater method may be adopted on the above mentioned gather portion of the absorbent article, and a spray method may be adopted around a urination portion of the absorbent article for which both an absorbing ability and a skin care effect are required.

In the diaper 70 of this embodiment, the water-soluble skin care agent and oily skin care agent described above are applied on the waist flaps 30a, 30b, peripheral flaps 35a, 35b, regions 45a, 45b, and standing guards 60a, 60b; therefore, in the initiation stage of wearing the diaper 70, the oily skin care agent moves to regions around waist, regions around the body, groin and surrounding regions, and regions around the femoral, of a wearer, to manifest a skin care effect. Thereafter, the water-soluble skin care agent fixed under the oily skin care agent released when dissolved or dispersed in the presence of water derived from sweat and/or excretions, and moves (or is transferred) to the skin of a wearer, to manifest a skin care effect.

Therefore, in the diaper 70, rash of skin at regions around the waist, regions around the body, groin and surrounding regions, and regions around the femoral can be suppressed.

In the above mentioned diaper 70, a water-soluble skin care agent and oily skin care agent are applied on all gather portions; however, these skin care agents may be applied on only some gather portions. Further, it may also be permissible that an oily skin care agent and a water-soluble skin care agent are applied on some gather portions and either an oily skin care agent or a water-soluble skin care agent is applied only on some gather portions. From the standpoint of preventing rash of skin, it is preferable to apply them on at least the waist flap portion (waist gather portion).

It is also possible to apply a water-soluble skin care agent and oily skin care agent locally on the waist flaps 30a, 30b, peripheral flaps 35a, 35b, regions 45a, 45b, and standing guards 60a, 60b, in stead of application thereof on the whole body of them. In both the case of application on the whole body and the case of local application, it is preferable to select the application form of these skin care agents so that at least a part of the oily skin care agent is present on the side of the skin of a wearer after wearing the absorbent article before the water-soluble skin care agent is transferred to the skin of a wearer.

When a skin care agent is locally applied on the waist flaps 30a, 30b, peripheral flaps 35a, 35b, regions 45a, 45b, and standing guards 60a, 60b, specific examples of the distribution form of the application region include stripes, dots (island), lattice and the like.

Though the absorbent article mentioned in the embodiment is an expansion type diaper, the absorbent article of the present invention may also be a pants type diaper. It may also be an absorbent article other than diapers, providing it has a gather portion, such as sanitary napkins, incontinence pad, panty liners, vaginal discharge sheets and the like.

For example, in pants type diapers, since the above mentioned outer layer sheet has regions on which a waist flap, peripheral flap and leg gather are formed, the above mentioned water-soluble skin care agent and oily skin care agent are applied on desired portions among these portions.

Each sheet used as a material of an absorbent article is formed of a non-woven fabric in many cases. In applying (fixing) the above mentioned water-soluble skin care agent or oily skin care agent on non-woven fabric, the type of fiber constituting the non-woven fabric is not particularly restricted, and may be semi-synthetic fiber such as rayon, Lyocell and the like, synthetic fiber comprising a single fiber made of a thermoplastic resin such as polyethylene, polypropylene, polyethylene terephthalate, polyacrylic acid, polyamide and the like, and a complex fiber of a core-sheath type or side by side type, and the like, and also, a natural fiber such as pulp, cotton and the like.

Fiber constituting non-woven fabric may be used singly or in combination, and each fiber may be in any form of a long fiber or short fiber. Further, the fineness of fiber is also not particularly restricted, and can be appropriately selected depending on the application, grade and the like of the intended absorbent articles; however, the fineness of fiber used in the above mentioned inner sheet and surface sheet is preferably from about 0.5 to 8.9 dtex, more preferably from about 1 to 5.6 dtex.

The standing guard may be formed also by using a sheet made of other members than that of these surface sheet 11 and side sheet 13, in addition to formation using the surface sheet 11 and side sheet 13 as in the diaper 70 of the present embodiment.

In addition to a water-soluble skin care agent, a friction reducing agent can also be adhered to a diaper for the purpose of suppressing injuring of skin. As the friction reducing agent, a crystal in the form of a plate made of an organic substance, and organic fine particles can be used. As the above mentioned crystal in the form of a plate, listed are, for example, acylated taurine metal salts (lauroyltaurine calcium salt, lauroyl-β-alanyl calcium), distearyl ether, zinc sodium cetylphosphate, N-ε-lauroyl-L-lysine and the like, and as the above mentioned organic particles, for example, silicone beads, nylon beads, chitosan beads and the like.

In the water-soluble skin care agent application region, sweat suppressing agents such as aluminum hydroxy chloride, aluminum-zirconium salt, zinc p-phenolsulfonate and the like may also be applied, if necessary.

Second Embodiment

The feature of the diaper 70 in this embodiment is that a diamide derivative of the above mentioned formula (I) is applied on all of or a part of each inner surface (surface of side to be contacted with the skin of a wearer) of the surface sheet 11, waist flaps 30a, 30b, peripheral flaps 35a, 35b, and leg flaps 45a, 45b.

The above mentioned diamide derivative moves to the skin of a wearer on wearing of a diaper 70, and performs functions that (1) it suppresses direct contact of excretions with the skin of a wearer to suppress skin stimulus by the excretions, (2) it weakens friction of skin with the diaper to decrease skin stimulus by a diaper, (3) it improves the water retention ability and barrier function of a keratin layer after percutaneous absorption, working as an oily skin care agent. Therefore, in the diaper 70, rash of skin is suppressed.

As the abovementioned diamide derivative, it is preferable to use those having a viscosity at 36° C. of 5000 mPa·s or less, more preferably from 200 to 5000 mPa·s, even more preferably from 500 to 2000 mPa·s, or those of which viscosity is controlled to obtain such viscosity, from the standpoint of efficient movement of the diamide derivative to the skin of a wearer. By using a diamide derivative having a viscosity as described above, the oily skin care agent can be effectively moved to the skin of a wearer. That is, when the viscosity of a diamide derivative is 5000 mPa·s or less, the property of moving to the skin becomes extremely excellent, and there is no need to use an oily skin care agent in a large amount for realizing a predetermined rash suppressing effect. Further, an influence on absorbability decreases. When the viscosity of an oily skin care agent is 200 mPa·s or more, movement of the above mentioned diamide derivative to other sites can be effectively prevented even in the case of preservation over a long period of time of an absorbent article before wearing; as a result, a predetermined skin care effect is obtained effectively.

"Viscosity of a diamide derivative" in the present invention was measured by the same measuring method as used for the viscosity of an oily skin care agent in the above mentioned first embodiment.

The diamide derivative used in the present invention preferably shows a smaller dependency of viscosity on temperature. Specifically, preferable are those having a viscosity at 36° C. within the above mentioned range and a viscosity at 80° C. of from 50 to 200 mPa·s. When dependency of viscosity on temperature is small, a diamide derivative can be uniformly applied easily on a sheet, and it is stably fixed on a sheet even if some temperature change occurs; consequently, there is a scarce tendency of the occurrence of absorption disturbance by penetration or diffusion of a diamide derivative into an absorber. Application of a diamide derivative on an absorbent article or its material can be conducted by the same application method as for an oily skin care agent in the above mentioned first embodiment.

It is preferable to select the application amount of a diamide derivative in view not only of an influence on the absorbing ability of an absorber but also its feeling to the skin and a skin care effect. For example, when a diamide derivative is applied continuously in the form of a film or layer, contact area with the skin of a wearer spreads; consequently, the amount of movement of a diamide derivative to the skin increases and skin is easily coated over a broader range, to enhance a skin care effect, while, the absorbing ability of an absorber may be decreased easily and a sticky feeling is generated in some cases.

In view of a skin care effect, feeling to the skin and the like, the application amount of a diamide derivative (meaning application amount in a region on which a diamide derivative is actually applied) is preferably in the range from about 0.05 to 20 g/m², more preferably in the range from about 0.1 to 10 g/m². Particularly in the case of application on a surface sheet, a range of from 0.1 to 5 g/m² is even more preferable. This application amount can be determined from a difference in weight of an application subject before and after application of a diamide derivative.

If necessary, two kinds of application methods may be used together in one absorbent article. For example, a dice coater method may be adopted for the absorbent article's which contacts with the wearer's buttock area for which a higher skin care effect is required, and a spray method may be adopted around the absorbent article's portion wherein the wearer urinates for which both an absorbing ability and a skin care effect are required.

When a diamide derivative is applied also on an absorber, the water absorption speed (JIS L 1096 (Japan Industry Standard), water-absorption, water-absorbing speed, method A (dropping method)) of a surface sheet can preferably be made to 10 seconds or less by controlling its application amount in the above mentioned range. Therefore, an absorbent article having a practical absorbing ability can be obtained.

The diamide derivative may be used singly or in a combination of two or more. If necessary, it can be used together with other oily skin care agents. As the other oily skin care agent, those having efficacies such as protection, cure and the like for the skin of a wearer can be used without specific restriction, and for example, those used as an emollient agent in the field of cosmetics can be used.

As the above mentioned other oily skin care agent, those oily skin care agents exemplified in the first embodiment can be used.

Though the absorbent article of the above mentioned embodiment is an expansion type diaper, the absorbent article of the present invention may also be a pants type diaper. In any of the expansion type diaper and pants type diaper, it is preferable to apply a diamide derivative of the formula (I) at least locally on an absorber or apply to coat the whole body of an absorber on plane view, from the standpoint of suppressing rash of skin.

In any of the expansion type diapers and pants type diapers, a diamide derivative of the above mentioned formula (I) can be applied on, for example, only the surface sheet 11, only the waist flaps 30a, 30b, only the peripheral flaps 35a, 35b or only the leg flaps 45a, 45b, and can also be applied on two or more positions. On the waist flaps, peripheral flaps and side flaps, it is preferable to apply a diamide derivative of the above mentioned formula (I) locally or on the whole surface thereof, particularly when a gather (waist gather, peripheral gather, or leg gather) is formed on these regions.

The absorbent article of the present invention is not limited to diapers and can be applied also to other absorbent articles such as sanitary napkins, incontinence pads, panty liners, vaginal discharge sheets and the like.

Each sheet used as a material of an absorbent article is formed of a non-woven fabric in many cases, and sheets of the same embodiment as shown in the above mentioned first embodiment can be used.

A surface sheet in a sanitary napkin is formed of a liquid-permeable porous film in some cases. Even if the surface sheet is formed of a porous sheet, it is possible to obtain the same technological effect as for each diaper in the above mentioned embodiments by applying a diamide derivative of the formula (I) locally on this surface sheet or so as to cover the surface sheet, if necessary, using a water-soluble skin care agent with the diamide derivative.

Irrespective of the kind of material of an application subject, by using a diamide derivative of the formula (I) together with silicone, it becomes easy to reduce friction of an absorbent article with the skin of a wearer and it becomes easy to suppress stickiness caused by the diamide derivative. Further, silicone can function as a releasing agent in applying a diamide derivative. The use amount of silicone can preferably be from about 0.1 to 5 parts by weight based on 100 parts by weight of a diamide derivative of the formula (I). As the silicone, those of any condition and nature such as a liquid and solid can be used, and in the case of a liquid, those preferably having a viscosity of from about 5 to 10000 mPa·s, more preferably from 10 to 1000 mPa·s are suitable. When silicone is also used, it is preferable that the above mentioned diamide derivative is provided as a mixture with silicone on an absorbent article, and it is preferable that the viscosity of this mixture is about 5000 mPa·s or less, more preferably from 200 to 5000 mPa·s, even more preferably from 500 to 2000 mPa·s at 36° C.

Irrespective of use or no use of silicone, a friction reducing agent can be adhered to an absorbent article for the purpose of suppressing injuring of skin. As the friction reducing agent, the same agents as shown in the above mentioned first embodiment can be used.

If necessary, sweat suppressing agents such as aluminum hydroxy chloride, aluminum-zirconium salt, zinc p-phenolsulfonate and the like can also be applied.

The present invention has been explained above using embodiments believed to be most practical and preferable at the moment; however, the present invention is not limited to the embodiments disclosed in this specification, and can be appropriately altered in a range not contradicting the idea or subject of the present invention understood from claims and the whole specification, and it should be understood that absorbent articles having such alterations are also included in the technological range of the invention.

EXAMPLES

The following examples will specifically explain particular embodiments of the present invention. The examples are given solely for the purpose of illustration and are not to be construed as limitations of the present invention.

Example 1

An expansion type diaper was produced having the same constitution as that of the diaper 70 in the embodiment except that none of the water-soluble skin care agent and oily skin care agent is applied on the regions 45a, 45b (see FIG. 1A).

In this procedure, used as the surface sheet 11 was a non-woven fabric having basis weight of 30 g/m² obtained by using a core-sheath type complex fiber having a core component made of polypropylene and a sheath component made of polyethylene and having a fineness of 3.3 dtex. Before formation of a non-woven fabric, a liquid coating prepared by mixing hamamelis extract (1,3-butylene glycol extraction liquid) as a water-soluble skin care agent, polyoxyethylene sorbitan monolaurate (HLB=13.3) which is a hydrophilic surfactant, sorbitan tristearate (HLB=2.1) which is a hydrophobic surfactant, monoalkylphosphate potassium salt, an antistatic agent, a smoothing agent and the like was applied on the above mentioned core-sheath type complex fiber. In preparing the liquid coating, the addition amount of sorbitan tristearate was the same as the addition amount of polyoxyethylene sorbitan monolaurate. On the surface sheet 11, a water-soluble skin care agent is applied over the whole surface thereof.

After formation of the non-woven fabric, a diamide derivative of the following formula (II) was applied as an oily skin care agent on the waist flaps 30a, 30b. This diamide derivative is one of the diamide derivatives of the above-mentioned formula (I)

The application amount (fixation amount) of the above mentioned hamamelis extract is 0.07 wt %, the application amount (application amount at applied regions) of the above mentioned diamide derivative is 1.0 g/m², and the viscosity at 36° C. of the applied diamide derivative is 1800 mPa·s. Application of the diamide derivative was conducted under a temperature of 80° C. using a spray coater.

As the side sheets 13a, 13b, non-woven fabric having a basis weight of 15 g/m² formed of polypropylene fiber was used, and as the outer layer sheet 15, a liquid-impermeable gas-permeable film obtained by uniformly mixing linear low density polyethylene and calcium carbonate, then, extruding the mixture via a dice to obtain a film, and performing monoaxial drawing treatment on this film, and having a moisture permeability (according to JIS Z 0208—Japan Industry Standard) of 4800 g/m²·24 hours was used. As the absorber 20, a body was used obtained by mixing a high water-absorbing polymer and pulp at a weight ratio of 50:50 to obtain an absorbing material and covering this with a mounting.

Comparative Example 1

A diaper was produced in the same manner as in Example 1 except that an oily skin care agent was not applied on the waist flaps 30a, 30b.

<Evaluation of Diaper Rash Preventing Ability>

The diapers produced respectively in Example 1 and Comparative Example 1 were used by 10 monitors, and the relative occurrence frequency was measured when the rash occurrence frequency in Comparative Example 1 was 1. When this value is smaller, the rash preventing ability is higher as compared with the diaper in Comparative Example 1.

The results of the measurement of diaper rash occurrence frequency in each diaper are shown in Table 1 together with the application position and kind of a skin care agent applied on the diaper.

As is apparent from Table 1, the diaper produced in Example 1 was excellent in rash preventing ability as compared with the diaper produced in Comparative Example 1.

Example 2

<Test 1 for Ability of Suppressing Occurrence of Erythema>

Using inside parts of the forearms (both arms) of five healthy adults, a patch test was conducted using a predetermined combination of the water-soluble skin care agent and oily skin care agent shown in Table 2, and a test was conducted on its ability of suppressing the occurrence of erythema. As the oily skin care agent of sample No. 2, a monoamide compound of the following formula (III) (viscosity at 36° C. was 1000 mPa·s) was used.

First, a predetermined position inside of the forearm was cleaned with an acetone/ether (1:1) solution, and a non-woven fabric on which an oily skin care agent had been applied at a proportion of 1.0 g/m² was placed under a pressure of 4.4 kPa. Thereafter, an adhesive tape for a patch test soaked with a water-soluble skin care agent and ammonia 1.5 mass % physiological saline (100 μl) was pasted on the same position for 1.5 hours. After removal of the adhesive tape, it was left for 30 minutes, and the condition of the occurrence of erythema was confirmed by visual determination at four stages (0: no erythema, 1: slight 2: somewhat red, 3: red). The average values (level of severity of erythema) of the condition of the occurrence of erythema are shown in Table 2.

TABLE 1

| | Surface sheet | Waist flap | Kind of water-soluble skin care agent | Kind of oily skin care agent | Rash occurrence frequency *3 |
|---|---|---|---|---|---|
| Example 1 | Water-soluble skin care agent | Water-soluble skin care agent + oily skin care agent *1 | Hamamelis extract | Diamide derivative *2 | 0.6 |
| Comparative Example 1 | Water-soluble skin care agent | Water-soluble skin care agent | Hamamelis extract | — | 1 |

*1: oily skin care agent was applied in the form of one band
*2: meaning a diamide derivative of the formula (II)
*3: showing relative value when the rash occurrence frequency in a diaper produced in Comparative Example 1 is 1

TABLE 2

| Sample No. | Water-soluble skin care agent | Oily skin care agent | Level of severity of erythema |
|---|---|---|---|
| 1 | Hamamelis extract | Diamide of the formula (II) | 1.6 |
| 2 | Hamamelis extract | Monoamide of the formula (III) | 1.2 |
| 3 | Hamamelis extract | Vaseline | 1.2 |
| 4 | Hamamelis extract | None | 2.0 |
| 5 | None | Diamide of the formula (II) | 1.8 |

As apparent from Table 2, it was confirmed that the occurrence of erythema can be suppressed effectively using a combination of an oily skin care agent and a water-soluble skin care agent of an embodiment of the present invention than in the single use of an oily skin care agent or a water-soluble skin care agent.

Example 3

<Test 2 for Ability of Suppressing Occurrence of Erythema>

Using inside parts of the forearms of thirteen healthy adults, a test was conducted on the ability of suppressing the occurrence of erythema by a water-soluble skin care agent shown in Table 3. First, a predetermined position inside of the forearm was cleaned with an acetone/ether (1:1) solution. Thereafter, an adhesive tape for a patch test soaked with an ammonia 2 mass % physiological saline (15 µl) and 15 µl of various plant extract 1% solution (1,3-butylene glycol extraction solution) (since peach leaf extract is a dry powder, only peach leaf extract: 0.01%) shown in Table 3 was pasted for 3 hours. After removal of the adhesive tape, it was left for 150 minutes, and the condition of the occurrence of erythema was confirmed by a visual determination at four stages. The ratio (B/A) of (A) a visual determination result of erythema in the case of using an adhesive tape soaked only with ammonia and (B) a visual determination result of erythema in the case of using each water-soluble skin care agent was measured for each member, and the number of adults showing this value less than 1 was divided by 13 (the number of all adults) to give a value as the anti-inflammation score. The results are shown in Table 3. It is shown that when the anti-inflammation score is high, the effect of suppressing the occurrence of erythema is high.

TABLE 3

| Sample No. | Water-soluble skin care agent | Anti-inflammation score |
|---|---|---|
| 6 | Hamamelis extract | 0.42 |
| 7 | Peach leaf extract | 0.16 |
| 8 | Citrus extract | 0.50 |
| 9 | Eucalyptus extract | 0.18 |
| 10 | Hiba arborvitae extract | 0.38 |

As apparent from Table 3, it was confirmed that in the case of using any water-soluble skin care agent, the occurrence of erythema is effectively suppressed as compared with the case of no use thereof, confirming that any agent has a high skin care effect. Therefore, it is supposed that the same skin care effect is performed even in the case of using these water-soluble skin care agents instead of hamamelis extract in Example 1 and Example 2 described above.

Example 4

An expansion type diaper having the same constitution as that of the diaper 70 in the second embodiment was produced using a diamide derivative of the following formula (II) which is one of the diamine derivatives of the above mentioned formula (I).

(II)

In this procedure, as the surface sheet 11, a non-woven fabric having a basis weight of 30 g/m² obtained by using a core-sheath type complex fiber having a core component made of polypropylene and a sheath component made of polyethylene and having a fineness of 3.3 dtex was used. The above mentioned diamide derivative was applied on the whole inner surface of this surface sheet 11, waist flaps 30a, 30b, and standing guards 60a, 60b by using a spray coater under a temperature condition of 80° C. The application amount (application amount at applied regions) of the above mentioned diamide derivative is 1.0 g/m², and the viscosity at 36° C. of the applied diamide derivative is 1800 mPa·s.

As the side sheets 13a, 13b, non-woven fabric having a basis weight of 20 g/m² formed of polypropylene fiber was used, and as the outer layer sheet 15, a liquid-impermeable gas-permeable film obtained by uniformly mixing a linear low density polyethylene and calcium carbonate, then, extruding the mixture via a dice to obtain a film, and performing mono-axial drawing treatment on this film, and having a moisture permeability (according to JIS Z 0208—Japan industry standard) of 4800 g/m²·24 hours was used. As the absorber 20, a body was used obtained by mixing a high water-absorbing polymer and pulp at a weight ratio of 50:50 to obtain an absorbing material and covering this with a mounting.

Comparative Example 2

A diaper was produced in the same manner as in Example 4 except that a diamide derivative was not applied.

<Evaluation of Diaper Rash Preventing Ability>

The diapers produced respectively in Example 4 and Comparative Example 2 were used by 10 monitors, and the relative occurrence frequency was measured when the rash occurrence frequency in Comparative Example 2 was 1. When this value is smaller, the rash preventing ability is higher as compared with the diaper in Comparative Example 2.

The results of measurement of diaper rash occurrence frequency in each diaper are shown in Table 4 together with the application position of a skin care agent applied on this diaper.

TABLE 4

| | Diamide derivative | | | | Rash generation frequency *2 |
|---|---|---|---|---|---|
| | Application position | | | | |
| | Surface sheet | Waist flap | Standing guard | Kind | |
| Example 4 | Application | Application | Application | Diamide derivative of formula (II) | 0.6 |
| Comparative Example 2 | No application | No application | No application | | 1 |

*1: used together with linear polysiloxane
*2: showing relative value when rash occurrence frequency of a diaper produced in Comparative Example 1 is 1

As apparent from Table 4, the diaper produced in Example 4 is excellent in rash preventing ability as compared with the diaper produced in Comparative Example 2.

(Effect of the Invention)

According to the present invention, an absorbent article is provided capable of suppressing rash of skin in regions at least around a gather portion. Therefore, according to the present invention, it becomes easy to provide an absorbent article having improved safety.

The invention claimed is:

1. An absorbent article comprising a liquid-impermeable outer layer sheet and an absorber fixed on the outer layer sheet, a gather portion having a flexible elastic member formed on a predetermined position, wherein the article has a substantially long shape, an abdomen side region, groin region and back side region for placing on a wearer's abdomen, a groin and back region for placing on a wearer while wearing respectively along it in the longitudinal direction, wherein an oily skin care agent is applied on a predetermined region of the absorbent article on which a water-soluble skin care agent is also applied, the water-soluble skin care agent is applied on an entirety of the surface to be contacted with the skin of a wearer of the gather portion, and the oily skin care agent is applied directly on the water-soluble skin care agent, such that at least a part of the oily skin care agent is able to be transferred to the skin of a wearer when worn before the water-soluble skin care agent is able to be transferred to the skin of the wearer, wherein the water-soluble skin care agent consists of a plant extract and the oily skin care agent consists of a diamide derivative of the following formula (I)

(I)

(wherein, $R^1$ represents a linear or branched hydrocarbon group having 1 to 22 carbon atoms optionally substituted with a hydroxy group and/or alkoxy group, $R^2$ represents a linear or branched divalent hydrocarbon group having 1 to 12 carbon atoms, and $R^3$ represents a linear or branched divalent hydrocarbon group having 1 to 42 carbon atoms, a linear or branched alkylene group having 11 to 42 carbon atoms or an alkenylene group having 1 to 4 double bonds).

2. The absorbent article according to claim 1, wherein leg opening portions are provided on both sides along the width direction of the groin region so that the width of the groin region is narrower than the maximum width of the back side region and abdomen side region, and the predetermined position includes a position adjacent to the leg opening portion along the width direction and the gather portion formed on each position is a leg gather portion formed by placing a flexible elastic member so that the leg opening portion can be placed around the leg of a wearer when wearing.

3. The absorbent article according to claim 1, wherein the predetermined position includes positions adjacent respectively to the left and right ends along the width direction of the absorber, and the gather portion formed on each position is a standing guard formed by placing a flexible elastic member along the longitudinal direction of the absorber.

4. A method of suppressing rash of skin, using the absorbent article according to claim 1.

5. The absorbent article according to claim 1, wherein a surfactant is applied together with the water-soluble skin care agent.

6. The absorbent article according to claim 1, wherein the water-soluble skin care agent is applied on the absorbent article by applying a liquid coating agent containing the water-soluble skin care agent and drying the liquid.

7. The absorbent article according to claim 1, wherein the absorbent article comprises a non-woven fabric, and wherein the water-soluble skin care agent is applied on the fibers of the non-woven fabric.

8. The absorbent article according to claim 1, wherein the predetermined position contains a longitudinal direction end of the abdomen side region or back side region, the gather portion formed at the longitudinal direction end is a waist gather portion formed by placing a flexible elastic member so as to extend along the width direction of the absorbent article.

* * * * *